United States Patent [19]

Jiang et al.

[11] Patent Number: 5,444,044
[45] Date of Patent: Aug. 22, 1995

[54] SYNTHETIC POLYPEPTIDES AS INHIBITORS OF HIV-1

[75] Inventors: Shibo Jiang; Kang Lin; A. Robert Neurath, all of New York, N.Y.

[73] Assignee: New York Blood Center, New York, N.Y.

[21] Appl. No.: 859,923

[22] Filed: Mar. 26, 1992

[51] Int. Cl.$^6$ ............ A61K 38/00; C07K 5/00; C07K 7/00; C07K 17/00
[52] U.S. Cl. ............................ 514/12; 530/300; 530/324; 530/350
[58] Field of Search ............ 530/300, 324, 350, 826; 514/12

[56] References Cited

FOREIGN PATENT DOCUMENTS

0330359A2  8/1989  European Pat. Off. .
0335134A2  10/1989  European Pat. Off. .
PCT/US87/-
01294  12/1987  WIPO .

OTHER PUBLICATIONS

Ratner, et al., "Complete Nucleotide Sequence of the AIDS Virus", *Nature,* vol. 313, pp. 277-284, (Jan. 24, 1985).

Neurath, et al., "B Cell Epitope Mapping of Human Immunodeficiency Virus Envelope Glycoproteins with Long (19- to 36-) Synthetic Peptides", *Journal of General Virology,* 71, pp. 85-95 (1990).

Neurath et al., Virology, vol. 188, pp. 1-13, 1992.

*Primary Examiner*—Jill Warden
*Assistant Examiner*—A. M. Davenport
*Attorney, Agent, or Firm*—Hoffmann & Baron

[57] ABSTRACT

A synthetic HIV-1-based polypeptide as well as methods for topically inhibiting HIV-1 infectivity or replication. The polypeptide of the present invention has an amino acid sequence substantially corresponding to a specified region of the HIV-1$_{IIIB}$ virus. The polypeptide of the present invention may be administered in effective amounts for topically inhibiting HIV-1 infectivity or replication. The polypeptide is useful for inhibiting the replication of the HIV-1 virus as well as HIV-1-mediated cytopathogenesis and cell fusion at levels which are within acceptable ranges of cytotoxicity.

20 Claims, 8 Drawing Sheets

SEQUENCE LISTING ( 1 ) GENERAL INFORMATION:

( i i i ) NUMBER OF SEQUENCES: 20

( 2 ) INFORMATION FOR SEQ ID NO: 1 :

( i ) SEQUENCE CHARACTERISTICS:
        ( A ) LENGTH: 30 Amino Acids
        ( B ) TYPE: Amino Acid
        ( D ) TOPOLOGY: Linear     ( x i ) SEQUENCE DESCRIPTION: SEQ ID NO: 1 :

```
Glu  Trp  Asp  Arg  Glu  Ile  Asn  Asn  Tyr  Thr  Ser  Leu  Ile  His
 1              5                   10                            15

Ser  Leu  Ile  Glu  Glu  Ser  Gln  Asn  Gln  Gln  Lys  Asn  Glu  Gln  Glu
                20                   25                           30
```

( 2 ) INFORMATION FOR SEQ ID NO: 2 :

( i ) SEQUENCE CHARACTERISTICS:
        ( A ) LENGTH: 30 Amino Acids
        ( B ) TYPE: Amino Acid
        ( D ) TOPOLOGY: Linear     ( x i ) SEQUENCE DESCRIPTION: SEQ ID NO: 2 :

```
Glu  Trp  Glu  Lys  Leu  Val  Asp  Asn  Tyr  Thr  His  Ile  Ile  Tyr  Thr  Leu
 1              5                   10                      15

Leu  Asp  Asp  Ala  Gln  Thr  Gln  Gln  Gly  Ile  Asn  Gln  Lys  Asp
      20                 25                      30
```

( 2 ) INFORMATION FOR SEQ ID NO: 3 :

( i ) SEQUENCE CHARACTERISTICS:
        ( A ) LENGTH: 30 Amino Acids
        ( B ) TYPE: Amino Acid
        ( D ) TOPOLOGY: Linear ( x i ) SEQUENCE DESCRIPTION: SEQ ID NO: 3 :

```
Glu Trp Asp Arg Glu Ile Ser Asn Tyr Thr Asn Thr Ile Phe Arg Leu
 1               5                  10                  15

Val Glu Asn Gly Gln Ile Gln Gln Asp Lys Asn Glu Arg Glu
            20                  25                  30
```

( 2 ) INFORMATION FOR SEQ ID NO: 4 :

( i ) SEQUENCE CHARACTERISTICS:
        ( A ) LENGTH: 30 Amino Acids
        ( B ) TYPE: Amino Acid
        ( D ) TOPOLOGY: Linear     ( x i ) SEQUENCE DESCRIPTION: SEQ ID NO: 4 :

```
Glu Trp Asp Arg Glu Ile Glu Asn Tyr Thr Gly Val Ile Trp Asn Leu
 1               5                  10                  15

Met Glu Lys Thr Gln Ser Gln Gln Asn Lys Asn Glu Leu Glu
            20                  25                  30
```

( 2 ) INFORMATION FOR SEQ ID NO: 5 :

( i ) SEQUENCE CHARACTERISTICS:
        ( A ) LENGTH: 30 Amino Acids
        ( B ) TYPE: Amino Acid
        ( D ) TOPOLOGY: Linear     ( x i ) SEQUENCE DESCRIPTION: SEQ ID NO: 5 :

```
Glu Trp Asp Arg Glu Ile Gln Asn Tyr Thr Gln Lys Ile His Gly Leu
 1               5                  10                  15

Ile Glu Gln Pro Gln Asn Gln Gln Gln Lys Asn Glu Gln Glu
            20                  25                  30
```

( 2 ) INFORMATION FOR SEQ ID NO: 6 :

( i ) SEQUENCE CHARACTERISTICS:
        ( A ) LENGTH: 30 Amino Acids
        ( B ) TYPE: Amino Acid
        ( D ) TOPOLOGY: Linear     ( x i ) SEQUENCE DESCRIPTION: SEQ ID NO: 6 :

```
Glu Trp Asp Arg Glu Ile Lys Asn Tyr Thr Asp Leu Ile His Asp Leu
 1               5                  10                  15

Ile Glu Arg Ser Gln Asn Gln Gln Lys Lys Asn Glu Gln Glu
            20                  25                  30
```

( 2 ) INFORMATION FOR SEQ ID NO: 7 :

( i ) SEQUENCE CHARACTERISTICS:
        ( A ) LENGTH: 30 Amino Acids
        ( B ) TYPE: Amino Acid
        ( D ) TOPOLOGY: Linear     ( x i ) SEQUENCE DESCRIPTION: SEQ ID NO: 7 :

```
Glu Trp Asp Arg Glu Ile Arg Asn Tyr Thr Glu Leu Ile His Glu Leu
 1               5                  10                  15

Ile Glu His Ser Gln Asn Gln Gln Arg Lys Asn Glu Gln Glu
            20                  25                  30
```

( 2 ) INFORMATION FOR SEQ ID NO: 8 :

( i ) SEQUENCE CHARACTERISTICS:
        ( A ) LENGTH: 30 Amino Acids
        ( B ) TYPE: Amino Acid
        ( D ) TOPOLOGY: Linear     ( x i ) SEQUENCE DESCRIPTION: SEQ ID NO: 8 :

```
Glu Trp Asp Arg Glu Ile His Asn Tyr Thr Lys Leu Ile His Gln Leu
 1               5                  10                  15

Ile Glu Ser Ser Gln Asn Gln Gln His Lys Asn Glu Gln Glu
```

(2) INFORMATION FOR SEQ ID NO: 9:

(i) SEQUENCE CHARACTERISTICS:
        (A) LENGTH: 30 Amino Acids
        (B) TYPE: Amino Acid
        (D) TOPOLOGY: Linear     (xi) SEQUENCE DESCRIPTION: SEQ ID NO: 9:

```
Glu Trp Asp Arg Glu Ile Thr Asn Tyr Thr Arg Leu Ile His Lys Leu
 1               5                  10                  15
Ile Glu Thr Ser Gln Asn Gln Gln Ser Lys Asn Glu Gln Glu
        20                  25                  30
```

(2) INFORMATION FOR SEQ ID NO: 10:

(i) SEQUENCE CHARACTERISTICS:
        (A) LENGTH: 30 Amino Acids
        (B) TYPE: Amino Acid
        (D) TOPOLOGY: Linear     (xi) SEQUENCE DESCRIPTION: SEQ ID NO: 10:

```
Glu Trp Asp Arg Glu Ile Asn Asn Tyr Thr Thr Leu Ile His His Leu
 1               5                  10                  15
Ile Glu Glu Ser Gln Asn Gln Gln Thr Lys Asn Glu Gln Glu
        20                  25                  30
```

(2) INFORMATION FOR SEQ ID NO: 11:

(i) SEQUENCE CHARACTERISTICS:
        (A) LENGTH: 33 Amino Acids
        (B) TYPE: Amino Acid
        (D) TOPOLOGY: Linear     (xi) SEQUENCE DESCRIPTION: SEQ ID NO: 11:

```
Glu Trp Asp Arg Glu Ile Asn Asn Tyr Thr Ser Leu Ile His Ser Leu
 1               5                  10                  15
Ile Glu Glu Ser Gln Asn Gln Gln Glu Lys Asn Glu Gln Glu Gly Gly
        20                  25                  30
Cys
```

(2) INFORMATION FOR SEQ ID NO: 12:

(i) SEQUENCE CHARACTERISTICS:
        (A) LENGTH: 33 Amino Acids
        (B) TYPE: Amino Acid
        (D) TOPOLOGY: Linear     (xi) SEQUENCE DESCRIPTION: SEQ ID NO: 12:

```
Glu Trp Glu Lys Leu Val Asp Asn Tyr Thr His Ile Ile Tyr Thr Leu
 1               5                  10                  15
Leu Asp Asp Ala Gln Thr Gln Gln Gly Ile Asn Gln Lys Asp Gly Gly
        20                  25                  30
Cys
```

(2) INFORMATION FOR SEQ ID NO: 13:

(i) SEQUENCE CHARACTERISTICS:
        (A) LENGTH: 33 Amino Acids
        (B) TYPE: Amino Acid
        (D) TOPOLOGY: Linear     (xi) SEQUENCE DESCRIPTION: SEQ ID NO: 13:

```
Glu Trp Asp Arg Glu Ile Ser Asn Tyr Thr Asn Thr Ile Phe Arg Leu
 1               5                  10                  15
Val Glu Asn Gly Gln Ile Gln Gln Asp Lys Asn Glu Arg Glu Gly Gly
        20                  25                  30
Cys
```

(2) INFORMATION FOR SEQ ID NO: 14:

(i) SEQUENCE CHARACTERISTICS:
        (A) LENGTH: 33 Amino Acids
        (B) TYPE: Amino Acid
        (D) TOPOLOGY: Linear     (xi) SEQUENCE DESCRIPTION: SEQ ID NO: 14:

```
Glu Trp Asp Arg Glu Ile Glu Asn Tyr Thr Gly Val Ile Trp Asn Leu
 1               5                  10                  15
Met Glu Lys Thr Gln Ser Gln Gln Asn Lys Asn Glu Leu Glu Gly Gly
             20                  25                  30
Cys
```

(2) INFORMATION FOR SEQ ID NO: 15:

(i) SEQUENCE CHARACTERISTICS:
        (A) LENGTH: 33 Amino Acids
        (B) TYPE: Amino Acid
        (D) TOPOLOGY: Linear     (xi) SEQUENCE DESCRIPTION: SEQ ID NO: 15:

```
Glu Trp Asp Arg Glu Ile Gln Asn Tyr Thr Gln Lys Ile His Gly Leu
 1               5                  10                  15
Ile Glu Gln Pro Gln Asn Gln Gln Lys Asn Glu Gln Glu Gly Gly
             20                  25                  30
Cys
```

(2) INFORMATION FOR SEQ ID NO: 16:

(i) SEQUENCE CHARACTERISTICS:
        (A) LENGTH: 33 Amino Acids
        (B) TYPE: Amino Acid
        (D) TOPOLOGY: Linear     (xi) SEQUENCE DESCRIPTION: SEQ ID NO: 16:

```
Glu Trp Asp Arg Glu Ile Lys Asn Tyr Thr Asp Leu Ile His Asp Leu
 1               5                  10                  15
Ile Glu Arg Ser Gln Asn Gln Gln Lys Lys Asn Glu Gln Glu Gly Gly
             20                  25                  30
Cys
```

(2) INFORMATION FOR SEQ ID NO: 17:

(i) SEQUENCE CHARACTERISTICS:
        (A) LENGTH: 33 Amino Acids
        (B) TYPE: Amino Acid
        (D) TOPOLOGY: Linear     (xi) SEQUENCE DESCRIPTION: SEQ ID NO: 17:

```
Glu Trp Asp Arg Glu Ile Arg Asn Tyr Thr Glu Leu Ile His Glu Leu
 1               5                  10                  15
Ile Glu His Ser Gln Asn Gln Gln Arg Lys Asn Glu Gln Glu Gly Gly
             20                  25                  30
Cys
```

(2) INFORMATION FOR SEQ ID NO: 18:

(i) SEQUENCE CHARACTERISTICS:
        (A) LENGTH: 33 Amino Acids
        (B) TYPE: Amino Acid
        (D) TOPOLOGY: Linear     (xi) SEQUENCE DESCRIPTION: SEQ ID NO: 18:

```
Glu Trp Asp Arg Glu Ile His Asn Tyr Thr Lys Leu Ile His Gln Leu
 1               5                  10                  15
Ile Glu Ser Ser Gln Asn Gln Gln His Lys Asn Glu Gln Glu Gly Gly
             20                  25                  30
```

Cys (2) INFORMATION FOR SEQ ID NO: 19:

(i) SEQUENCE CHARACTERISTICS:
    (A) LENGTH: 33 Amino Acids
    (B) TYPE: Amino Acid
    (D) TOPOLOGY: Linear (xi) SEQUENCE DESCRIPTION: SEQ ID NO: 19:

```
Glu Trp Asp Arg Glu Ile Thr Asn Tyr Thr Arg Leu Ile His Lys Leu
 1               5                  10                      15

Ile Glu Thr Ser Gln Asn Gln Gln Ser Lys Asn Glu Gln Glu Gly Gly
            20                  25                  30

Cys
```

(2) INFORMATION FOR SEQ ID NO: 20:

(i) SEQUENCE CHARACTERISTICS:
    (A) LENGTH: 33 Amino Acids
    (B) TYPE: Amino Acid
    (D) TOPOLOGY: Linear (xi) SEQUENCE DESCRIPTION: SEQ ID NO: 20:

```
Glu Trp Asp Arg Glu Ile Asn Asn Tyr Thr Thr Leu Ile His His Leu
 1               5                  10                      15

Ile Glu Glu Ser Gln Asn Gln Gln Thr Lys Asn Glu Gln Glu Gly Gly
            20                  25                  30

Cys
```

SYNTHETIC POLYPEPTIDES AS INHIBITORS OF HIV-1

This invention was made with Government support under CA 43315 and 5RD1 AI29373 awarded by the NIH. The Government has certain rights in the invention.

BACKGROUND OF THE INVENTION

The present invention generally relates to antiviral agents useful for inhibiting the infectivity of human acquired immunodeficiency virus. More particularly, the present invention concerns synthetic polypeptides capable of inhibiting the infectivity of HIV-1.

Acquired Immunodeficiency Syndrome (AIDS), caused by the HIV-1 virus, has been reported in increasing numbers throughout the world. The disease is currently recognized by medical experts as approaching epidemic proportions and there is presently no cure or vaccine available to control its spread. Furthermore, new strains are developing due to the high mutation rate of the virus. Consequently, there is a tremendous need for methods of treating HIV-infected individuals and for the prevention of HIV-1 infections.

Until recently, research efforts directed toward developing anti-HIV agents has focused on several approaches. These approaches include: (1) the development of polyclonal or monoclonal antibodies to HIV antigens; (2) chemical antiviral agents; and (3) a soluble CD4 molecule corresponding to the HIV receptor on CD4+ target cells.

For example, previous research efforts have yielded both monoclonal and polyclonal antibodies to various HIV proteins. In particular, envelope glycoproteins of the HIV-1 virus, such as gp160, have been found to elicit antibodies which neutralize the infectivity of HIV-1. Consequently, gp160 and various fragments thereof have been tested extensively as candidates for a potential vaccine against HIV-1 infections. Unfortunately, it has been found that some of the immunodominant regions present on gp160 elicit the production of harmful antibodies which may trigger undesirable immunosuppression or even enhance HIV-1 infections.

For example, it is well-known that gp160 is a glycosylated polypeptide which has a molecular weight of 160,000 daltons and is processed to yield envelope glycoproteins gp120 and gp41. Although gp120 and gp41 both elicit immune responses which result in antibodies to HIV-1, these responses are generally immunospecific to individual sub-types of the virus or may cause undesirable immunosuppressive effects. In particular, certain selected regions from gp120 and gp41 can suppress lymphocyte blastogenic responses and inhibit the activity of natural killer T-cells. Furthermore, some of the immunodominant regions of gp120 and gp41 do not contribute to protective immunity and may behave as immunological decoys.

An additional problem is encountered in developing a vaccine which is effective against HIV-1 infections because the virus exhibits frequent sequence variations during replication. More specifically, individual HIV-1 virus isolates demonstrate sequence variations, particularly in critical immunodominant regions of the virus sequence. Consequently, most virus-neutralizing antibodies are immuno-specific to individual clinical sub-types of the virus and the antibodies elicited by a vaccination against one clinical sub-type would likely be ineffective against another strain of the virus.

Other research efforts have been directed toward developing chemical agents which are effective against HIV-1 infections. For example, 3'azido-3'deoxythymidine (AZT) and other dideoxynucleoside analogs have been used to treat HIV-1 infections, however, these drugs are used in dosages which are often toxic to the patient. Furthermore, the use of chemical agents frequently induces the formation of viral mutants that are drug-resistant. Viral replication of drug-resistant mutants is not effectively inhibited by these drugs.

Additional research efforts have been directed toward the development of synthetic molecules containing receptor sites that mimic the receptor sites on target cells which the HIV-1 virions use to attach themselves to the cell membrane. For example, the CD4 molecule was expected to become the most hopeful anti-HIV agent for both therapy and prophylaxis of HIV-1 infections since it effectively inhibited viral replication in vitro. Unfortunately, it was later discovered that the molecule was not capable of inhibiting the infectivity of many clinical sub-types or strains of the virus.

It is therefore an object of the present invention to provide an antiviral substance which is capable of effectively inhibiting the replication of HIV-1, HIV-1-mediated cytopathogenesis and cell fusion at a concentration which falls within acceptable limits of cytotoxicity.

It is a further object of the present invention to provide an antiviral substance which is not specific to only one sub-type of HIV-1, but is effective against a variety of sub-types or strains of the virus.

It is still a further object of the present invention to provide an antiviral substance which is effective against AZT-resistant variants of HIV-1.

It is also an object of the present invention to provide a method of treating HIV-1 infections in a subject without inducing undesirable immunosuppressive effects.

SUMMARY OF THE INVENTION

The present invention provides a synthetic HIV-1-based polypeptide which comprises an amino acid sequence substantially corresponding to the amino acid sequence of the envelope glycoprotein of HIV-1$_{IIIB}$ virus from the amino acid residue 600 to amino acid residue 862, and most preferably from amino acid residue 637 to amino acid residue 666.

Additionally, the present invention also provides a method for treating a test subject infected with HIV-1 virus. The method involves administering to the subject an effective amount of the synthetic HIV-1-based polypeptide of the present invention in order to inhibit replication of the virus.

The polypeptide of the present invention includes an amino acid sequence which substantially corresponds to a portion of the amino acid sequence of the HIV-1 virus containing a domain that is critical to the ability of the virus to infect cells. This domain appears to be common to most clinical sub-types of HIV-1. Consequently, the present invention provides an antiviral substance specific to HIV-1 infections which is effective against variants and sub-types of the virus, especially those variants which have become resistant to chemical antivirals such as AZT.

Unlike the chemical antivirals currently available for treating HIV-1 infections, the present invention provides a method of effectively treating HIV-1 infected individuals while avoiding some of the undesirable physiological side effects associated with treatments using AZT or other similar substances. Additionally, the present invention provides both a method of treating HIV-1 infected individuals as well as a new antiviral substance against HIV-1 which does not induce undesirable side effects.

Moreover, low cytotoxicity and high antiviral activity are also important factors to be considered when evaluating an antiviral substance. For example, there are many chemical antiviral agents capable of inhibiting viral replication of HIV-1, but most of them are unacceptable due to high levels of cytotoxicity. The polypeptide of the present invention is quite advantageous as it falls within acceptable ranges of cytotoxicity while effectively inhibiting HIV-1 infection.

For a better understanding of the present invention, together with other and further objects, reference is made to the following description as well as the accompanying sequence listing and drawings, the scope of which will be pointed out in the appended claims.

DETAILED DESCRIPTION OF PREFERRED EMBODIMENTS

The present invention provides for a synthetic polypeptide which effectively inhibits infectivity and viral replication of HIV-1. As previously mentioned, the polypeptide of the present invention has an amino acid sequence substantially corresponding to the amino acid sequence of the envelope glycoprotein of the HIV-1$_{IIIB}$ virus from amino acid residue 600 to amino acid residue 862, and more preferably from amino acid residue 620 to 680. In the most preferred embodiment, the polypeptide is present as a dimer and has an amino acid sequence substantially corresponding to the amino acid sequence of the envelope glycoprotein of the HIV-1$_{IIIB}$ virus from amino acid residue 637 to 666. Additionally, the synthetic polypeptide of the present invention preferably includes a Gly-Gly-Cys amino acid triplet coupled at its C-terminus, thereby facilitating dimerization or alternatively affording a means for coupling the polypeptide to other entities.

It is known in the art of protein chemistry that an identical copy of a particular polypeptide can be readily produced where every amino acid in the copy appears in exactly the same sequential position as it does in the original. In short, the copy has an amino acid sequence which corresponds exactly to the amino acid sequence of the original polypeptide from which it was copied. Alternatively, certain amino acids in the copy can be substituted with natural or synthetic analogs without altering any of the desired biological characteristics of the resulting polypeptide, provided that the regions containing biologically important residues are conserved. For example, certain synthetic amino acid analogs can be substituted at desired positions within an amino acid sequence to impart resistance to proteolytic cleavage while maintaining the desired immunological character of the resulting polypeptide. Therefore, an identical copy of a particular polypeptide can receive certain substitutions at non-conserved regions and still retain the same biological character as the original polypeptide from which it was copied.

Generally, the synthetic peptide of the present invention can be substituted with natural or synthetic analogs as long as the regions responsible for the biological character of the peptide remain conserved. These substitutions may be induced to impart a desired a character to the resulting polypeptide or, alternatively, may occur as natural variations in the sequence as observed in identified sub-types of HIV-1. For example, each clinical isolate of the HIV-1 virus has its own variant sequence and it is known in the art that the relative numerical alignment of the amino acid sequences for each isolate will be slightly different.

Reconciliation of these differences during attempts to fashion polypeptides of the present invention after regions of interest in a particular isolate of HIV-1 can be readily accomplished using techniques known in the art. Accordingly, for purposes of the present application, the polypeptide of the present invention can be said to "substantially correspond with" the original polypeptide or isolate from which it was copied despite natural variations in sequence and/or numerical alignment or substitutions as discussed above.

In constructing the polypeptide of the present invention, a numerical frame of reference or standardized reading frame corresponding to the amino acid sequence of the envelope glycoprotein of HIV-1$_{IIIB}$ should be consulted in order to establish the region of interest, amino acid residues 637–666. Several publications containing standardized amino acid sequence data for the HIV-1 virus are currently available. See, for example, Ratner, et al., "Complete nucleotide sequence of the AIDS virus," *Nature*, Volume 313, 277, (January, 1985). See also, "Human Retroviruses and AIDS 1991, A Compilation and Analysis of Nucleic Acid and Amino Acid Sequences," (Myers et al. Eds.), Theoretical Biology and Biophysics Group, Los Alamos National Laboratory, Los Alamos, N. Mex., USA.

Upon establishing the proper reading frame, the amino acid region of interest can be reproduced using a variety of procedures available in the art. For example, a variety of automated synthesis units are currently available including the NPS 4,000 semi-automated multichannel peptide synthesizer and the Biosearch Model 9,600 automatic peptide synthesizer. Alternatively, certain recombinant DNA techniques or proteolytic cleavage techniques may be incorporated for constructing the polypeptide of the present invention. For example, a carefully orchestrated proteolysis of gp160 or gp41 using proteolytic enzymes or chemical cleaving agents would be an acceptable method for producing a polypeptide of the present invention. Accordingly, the term "synthetic polypeptide", as it appears throughout the present Application, is taken to mean any non-naturally-occurring polypeptide constructed by one of the methods mentioned above or by other suitable methods known in the art.

The Sequence Listing portion of the present Application provides examples of several synthetic polypeptides having amino acid sequences substantially corresponding to the amino acid sequences of the envelope glycoprotein of various clinical isolates of HIV-1 virus from amino acid residue 637 to 666 (see SEQ ID NOS: 1-10). As previously mentioned, the polypeptide of the present invention may preferably contain a Gly-Gly-Cys amino acid triplet coupled to its C-terminus in order to facilitate dimerization or attachment to another entity. The Sequence Listing portion of the present Application also contains each of the amino acid sequences set forth in SEQ. ID NOS: 1-10 further comprising a Gly-Gly-Cys triplet coupled to its C-terminus (see SEQ ID NOS: 11-20). These amino acid sequences constitute various synthetic polypeptides constructed in accordance with the present invention.

In addition to the monomeric forms of the synthetic polypeptides set forth in the Sequence Listing portion of the present Application, the present invention also includes dimeric, trimeric and other polymeric forms of these peptides. In particular, the best mode of the present invention is the dimeric form of the polypeptide, wherein dimerization is achieved via the Gly-Gly-Cys triplet positioned at the C-terminus of the peptide, as illustrated in SEQ ID NOS. 11-20. Dimerization or polymerization of the polypeptide of the present invention can be induced using any number of acceptable methods known in the art.

For example, a variety of covalent chemical or physical linkages can be employed to produce multimers of the polypeptide of the present invention. In particular, multimers of the polypeptide can be generated via attachment to multimeric peptide carriers known in the art or other approaches, such as multiple antigen peptide systems (MAP) or ISCOM. Furthermore, in addition to inducing dimerization via the Gly-Gly-Cys triplet coupled to the C-terminus of the polypeptides illustrated in SEQ ID NOS. 11-20, additional cysteine residues found outside of the 637-666 region may be utilized to induce dimerization where the polypeptide to be dimerized has amino acid residues extending beyond residue 666.

In particular, dimerization or polymerization may be mediated through additional -Cys- groups incorporated in or attached to the polypeptide. Additionally, the polypeptides described herein may be coupled to protein or high molecular weight (macromolecular) polymeric carriers (or substrates) through several types of functional groups on the polypeptides. For example, thiol (—SH) groups, aromatic rings (e.g., Tyr or His), amino or carboxyl groups, etc. would be acceptable linking moieties. Methods designed to avoid the use of carriers by polymerizing synthetic polypeptides to give peptide polymers are also known in the art. Another particular approach, known as the multiple antigen peptide system (MAP), utilizes a small peptidyl core matrix with covalently attached, radially branching, multiple synthetic peptides. See, for example, Tam, J.P. (1988) "Synthetic Peptide Vaccine Design: Synthesis and Properties of a High-Density Multiple Antigenic Peptide System" *Proc. Natl. Acad. Sci. U.S.A.*, 85, 5409-5413.

As illustrated in the Examples below, the polypeptide of the present invention effectively inhibits infections of various cell lines, such as the monocytic cell line U937 and CD4+ T-cell lines MT-2 and H9, by several HIV-1 isolates, including the HIV-1 isolates MN, RF, SF2, IIIB and AZT-resistant isolates. In addition to effectively inhibiting HIV-1 viral replication, the polypeptide of the present invention provides for excellent inhibition of HIV-1-mediated cytopathogenesis and cell fusion, as compared with other synthetic polypeptides fashioned from other regions of the HIV-1 virus amino acid profile. Furthermore, the polypeptide of the present invention performs effective inhibitory function at acceptable levels of cytotoxicity.

The following Examples serve to further illustrate the present invention but are not meant in any way to limit or restrict the effective scope of invention.

EXAMPLE 1

In accordance with the present invention, 29 peptides covering almost the entire sequence of HIV-1$_{IIIB}$ gp160 and 21 peptides corresponding to the full-length V3 hypervariable loops of distinct HIV-1 isolates were synthesized. The syntheses were carried out on either an NPS 4000 semi-automated multichannel peptide synthesizer or a Biosearch Model 9600 automatic peptide synthesizer. The purity of the product was confirmed by HPLC and by amino acid analysis. The sequence of each peptide was determined using an Applied Biosystems Protein Sequence Model 477A with on-line HPLC analysis of PTH amino acids using an Applied Biosystems Model 120A PTH analyzer.

EXAMPLE 2

For virus inhibition assays, H9, MT-2 and U937 cells were used as target cells. Five HIV-1 isolates (IIIB, MN, RF, SF2, and an AZT-resistant mutant) were cultivated in MT-2 cells, collected, and aliquoted. The titer of infectivity of the virus stocks were $10^4$–$10^6$, 50% tissue culture infective doses(TCID$_{50}$).

HIV-1 infectivity was determined by two distinct methods; an ELISA measuring HIV-1 core protein p24 production and a colorimetric assay for HIV-mediated cytopathogenesis. Briefly, $1 \times 10^4$ MT-2 cells in 96 well plates were infected with dilutions of HIV-1$_{IIIB}$ in 200 μl RPMI 1640 medium with 10% FBS. After 24 hrs., half of the culture medium was changed. On the fourth day after incubation at 37° C., 100 μl of culture supernatant was collected from each well and an equal volume of fresh medium was added to the wells. The collected supernatants were mixed with equal volumes of 5% Triton X-100 and assayed for p24 using a kit from Coulter Immunology (Hialeah, Fla.). On the sixth day post infection, an indicator XTT tetrazolium dye (1 mg/ml; 50 μl/well; PolySciences, Inc., Warrington, Pa.) was added to the cells. After a 4 hr. period, intracellular formazan was determined colorimetrically at 450 nm. The percentage of cytopathogenesis was calculated using the following formula: [(OD$_{450}$ in negative control−OD$_{450}$ in experiment)/(OD$_{450}$ in negative control−OD$_{450}$ in positive control)]×100. The negative control corresponded to cells mixed with culture medium, instead of HIV, while the positive control represented cells mixed with 100 TCID$_{50}$ of HIV-1$_{IIIB}$ which lysed 100% of the MT-2 cells.

The inhibitory effect of the peptide of the present invention on the fusion of HIV-1 infected cells with uninfected cells was also determined. In brief, $1.25 \times 10^4$ HIV-1$_{IIIB}$ infected H9 cells were mixed with the peptide and an equal number of uninfected H9 cells. After incubation at 37° C. for 16 hrs., the syncytium-forming cells in a titer plate well were counted under a microscope and the inhibition of cell fusion by the peptide was calculated.

Figure 1:
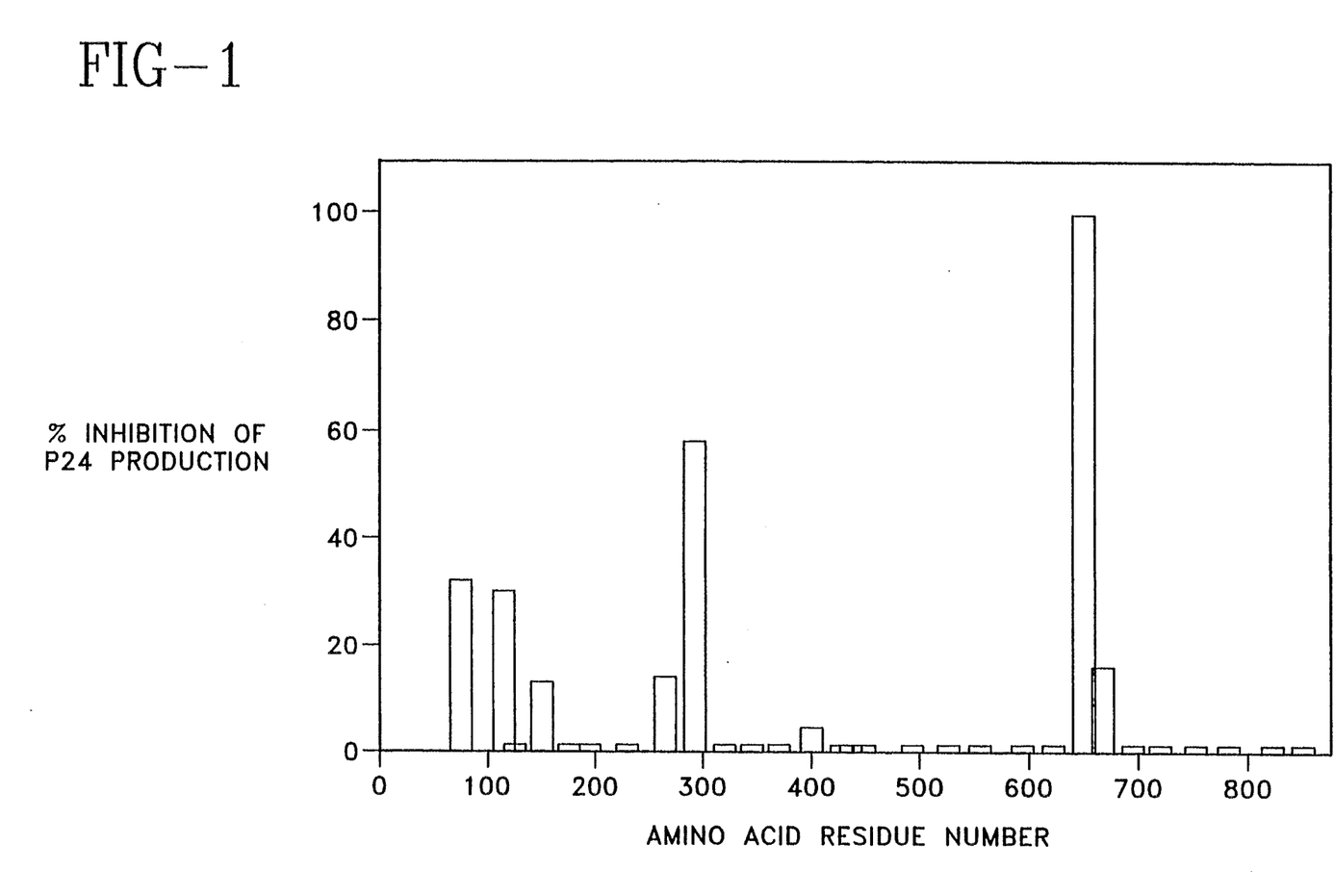
FIG. 1 illustrates the inhibition of HIV-1$_{IIIB}$ replication in MT-2 cells by synthetic peptides from gp120/gp41 of HIV-1$_{IIIB}$.

Twenty-nine peptides from HIV-1$_{IIIB}$ gp160 (gp120/gp41) and 21 peptides from V3 hypervariable loops of distinct HIV-1 isolates were screened for their inhibitory activity on HIV-1 replication and HIV-1-mediated cytopathogenesis in MT-2 cells. As shown in FIG. 1, among the 29 peptides from gp160 screened, four peptides (amino acid sequence 61–90, 102–126, 280–306, and 637–666), at a final concentration of 12.5 μg/ml, significantly inhibited HIV-1 replication, as indicated by a decrease of gag protein p24 synthesis. However, none of the peptides from V3 loops of 21 distinct HIV-1 isolates inhibited HIV-1 replication.

Figure 2:
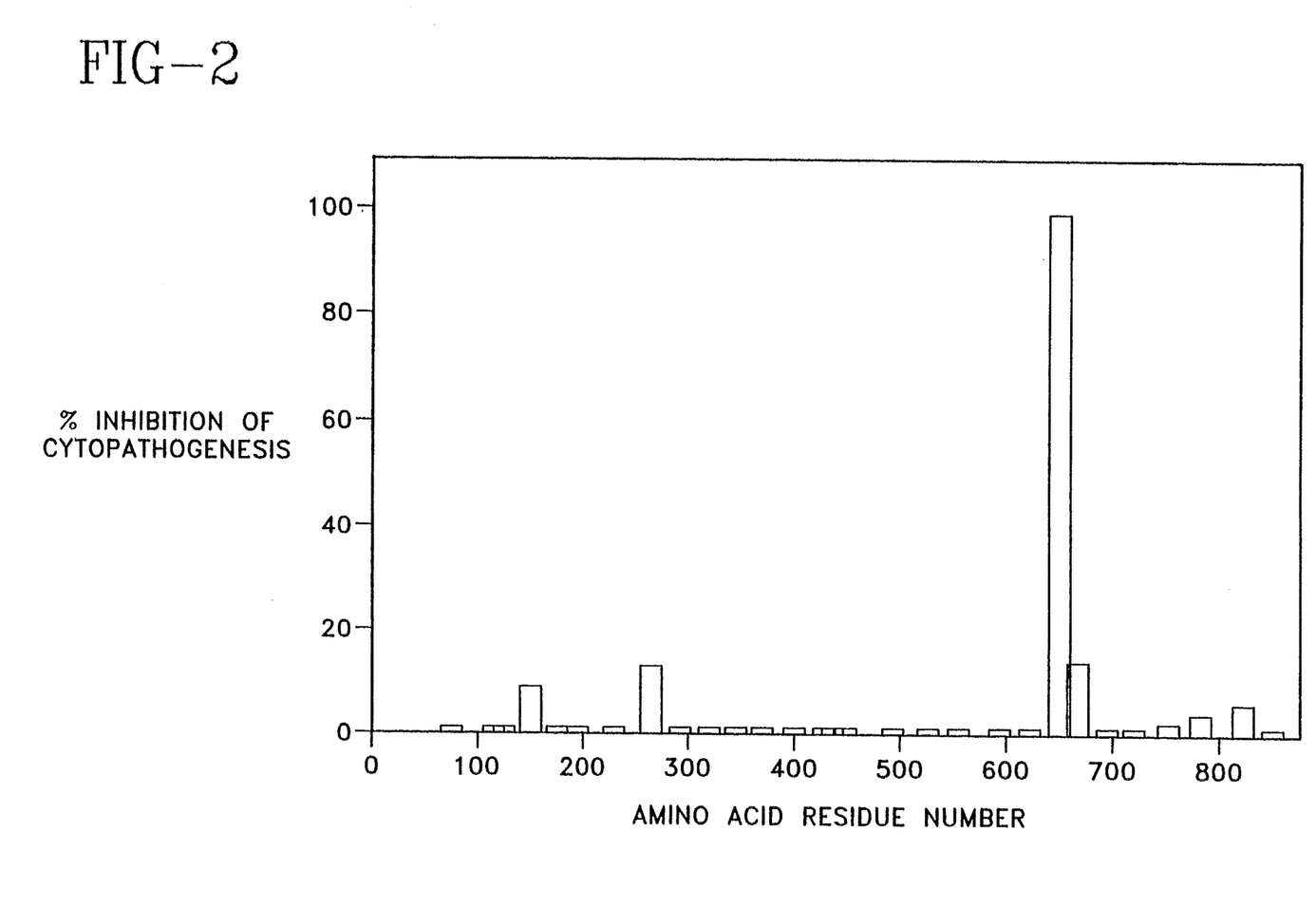
FIG. 2 illustrates the inhibition of HIV-1$_{IIIB}$-mediated cytopathogenesis in MT-2 cells by synthetic peptides from gp120/gp41 of HIV-1$_{IIIB}$.

Additionally, studies were performed to determine whether or not any of the peptides could inhibit the cytopathogenesis mediated by HIV-1. The results are shown in FIG. 2. Only the peptide (637–666) markedly inhibited cytopathogenesis, while the other three peptides which inhibited p24 production did not exhibit this inhibitory activity.

These results demonstrate that the peptide (637–666) from gp160 of HIV-1$_{IIIB}$ effectively inhibited infection by the homologous HIV-1 isolate (IIIB).

EXAMPLE 3

Figure 3:
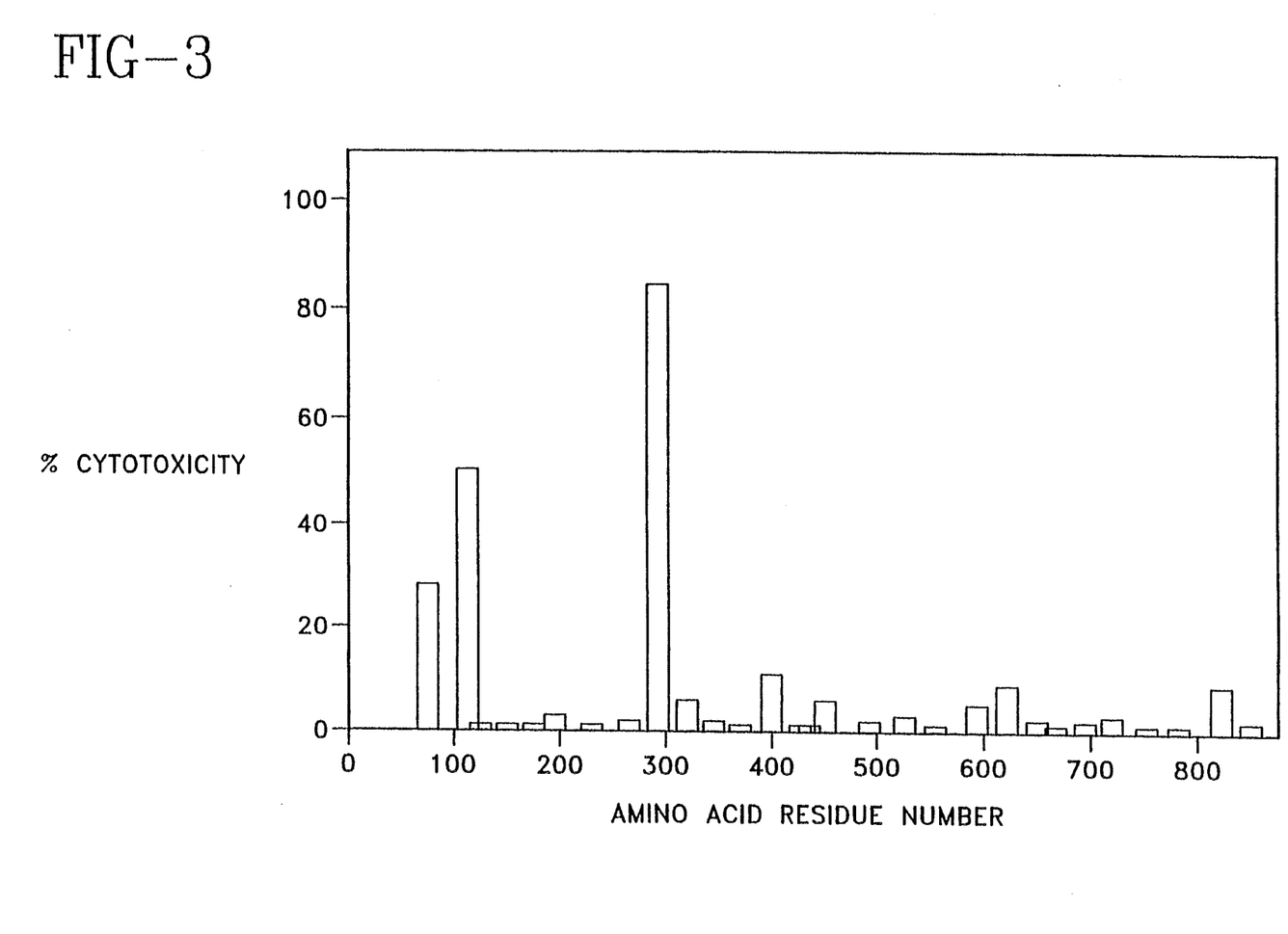
FIG. 3 illustrates cytotoxicity mediated by the various synthetic peptides.

Subsequently, cytotoxicity studies were performed using MT-2 cells at a final concentration of 12.5 μg/ml. It was found that three peptides (61–90, 102–126, and 280–306) had significant cytotoxicity, while the peptide (637–666) did not exhibit any cytotoxicity (see FIG. 3). When the concentration of the peptide (637–666) was increased to 11,145 μM, significant cytotoxicity remained undetectable. These results suggest that the inhibition of p24 production by the three peptides (61–90, 102–126, and 280–306) was actually due to the cytotoxicity of these peptides for MT-2 cells, while only the peptide (637–666) could really inhibit both p24 production and cytopathogenesis.

Figure 4:
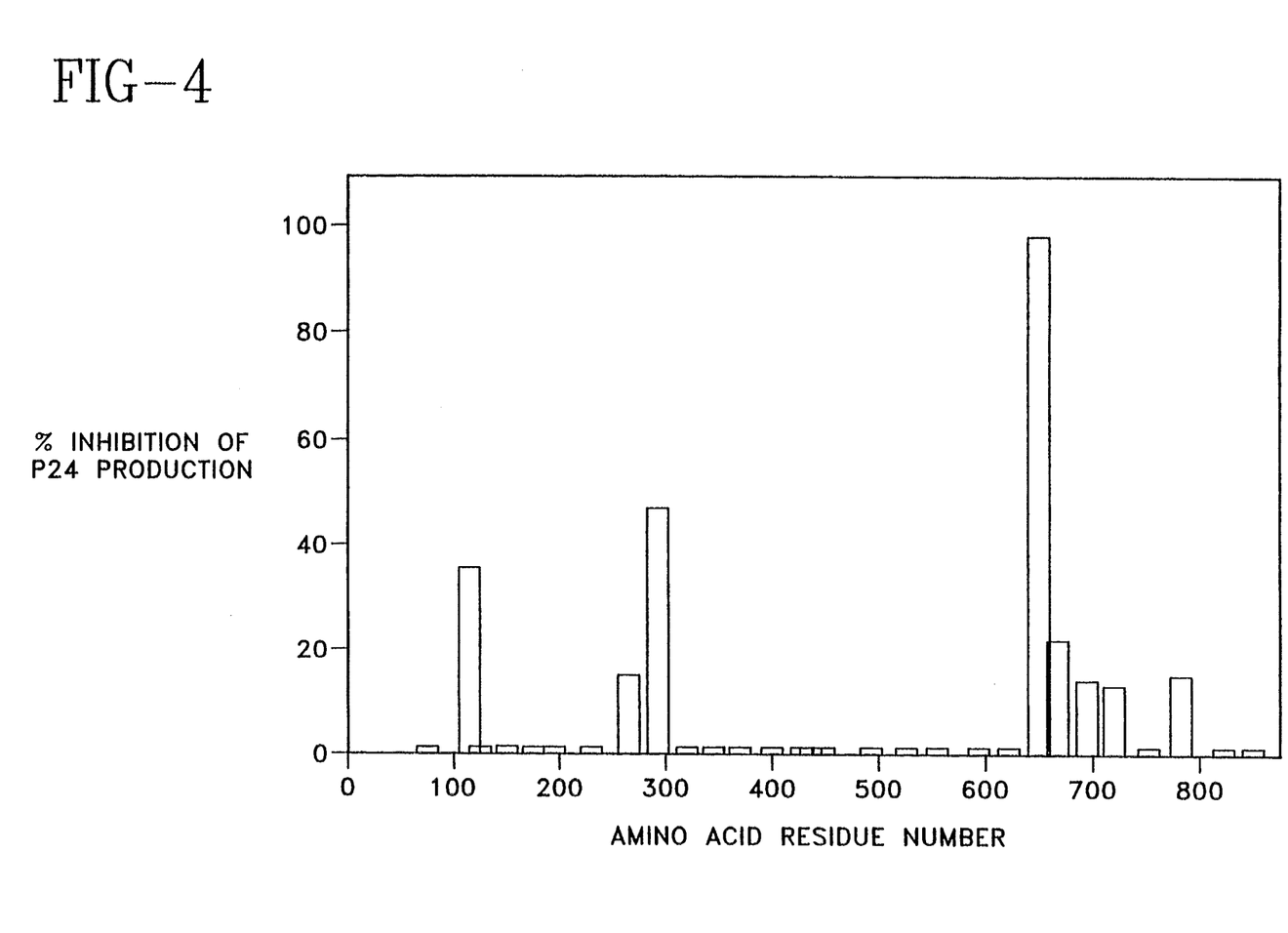
FIG. 4 illustrates the inhibition of HIV-1$_{IIIB}$ replication in U937 cells by synthetic peptides from HIV-1$_{IIIB}$ gp120/gp41.

The same techniques were also used to screen peptides with the monocytic cell line, U937. The results are shown in FIG. 4 Among the 29 peptides from gp160, only three peptides (102–126, 280–306 and 637–666) significantly inhibited p24 production. The peptide (637–666) had the highest inhibitory activity, suggesting that this peptide could inhibit the infection of both CD4+ T lymphocytes and of monocytic cells.

EXAMPLE 4

Figure 5:
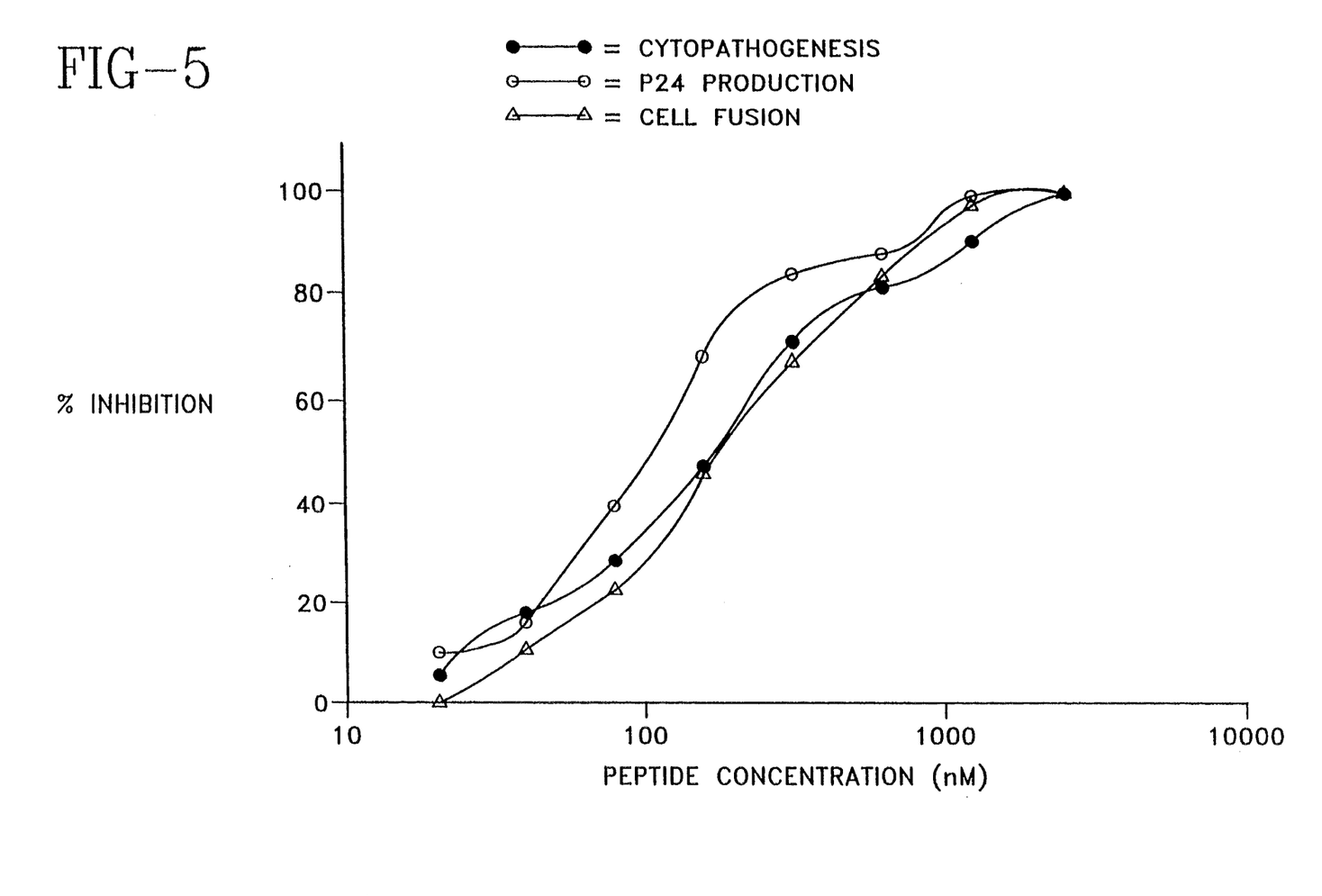
FIG. 5 illustrates the dose-dependent inhibition of HIV-1$_{IIIB}$ infection of MT-2 cells by synthetic peptide (637–666).

Subsequently, the peptide (637–666) was tested for its inhibitory activities on the HIV-1 replication, HIV-1-mediated cytopathogenesis and cell fusion at serial dilutions. As shown in FIG. 5, the peptide inhibited p24 production, cytopathogenesis and cell fusion in a dose-dependent manner. The ED$_{50}$ for inhibition of HIV-1$_{IIIB}$ replication, as indicated by the decrease of gag protein p24 production, was 101.0 nM; for inhibition of cytopathogenesis mediated by HIV-1$_{IIIB}$, 142.0 nM; and, for inhibition of cell fusion, 160.0 nM.

EXAMPLE 5

Figure 6:
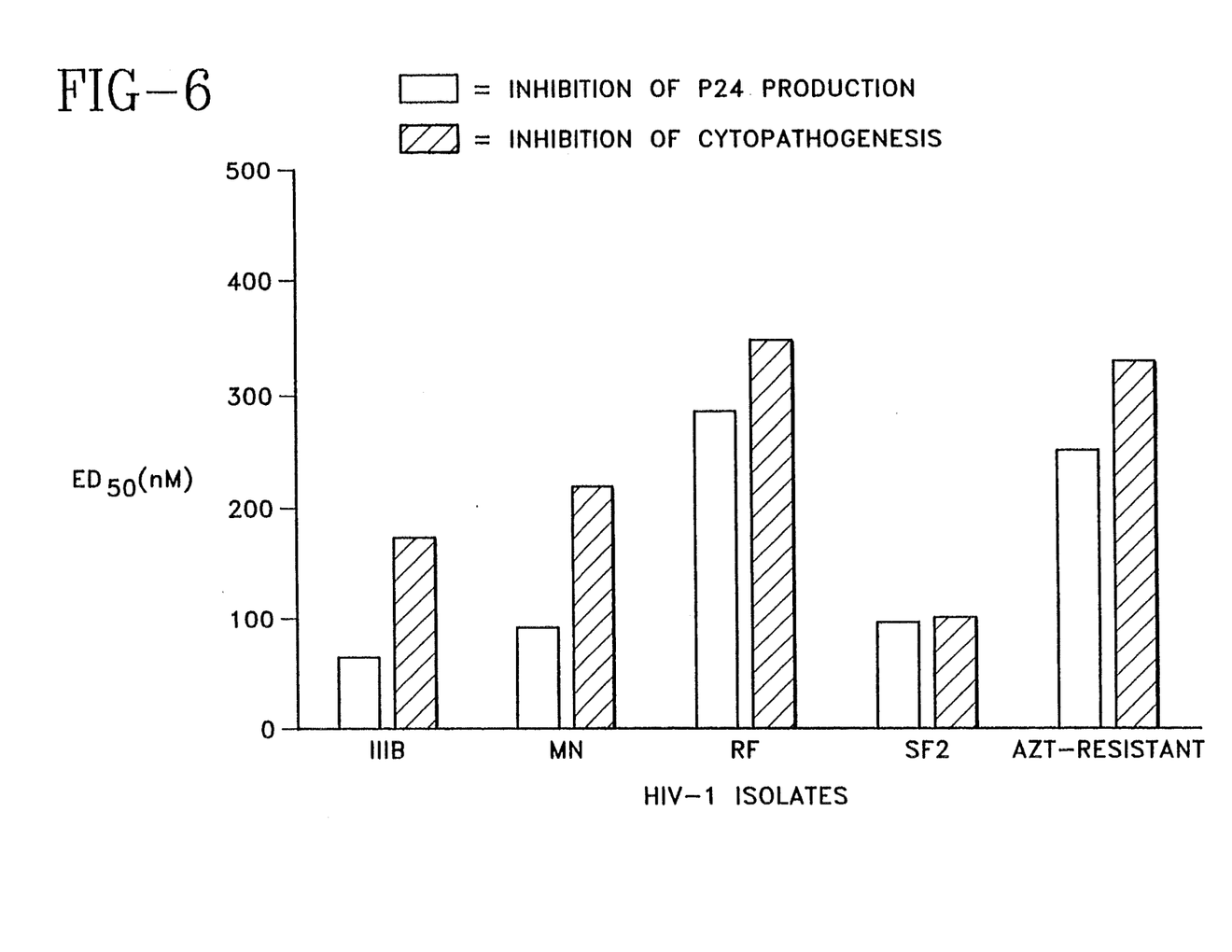
FIG. 6 illustrates the inhibition of various HIV-1 isolates by synthetic peptide (637–666).

Further studies were conducted to determine whether or not the peptide of the present invention would also inhibit the replication of other HIV-1 isolates, such as MN, RF and SF2 isolates, as well as an AZT-resistant mutant. Results are shown in FIG. 6. The peptide (637–666) effectively inhibited infections by all the five HIV-1 isolates, although the ED$_{50}$ for inhibition of both replication and cytopathogenesis mediated by the distinct HIV-1 isolates were different. These results suggest that the anti-HIV activity of the peptide (637–666) is not sub-type (isolate) limited. Furthermore, the peptide is also effective against AZT-resistant HIV-1 isolates.

EXAMPLE 6

Figure 7:
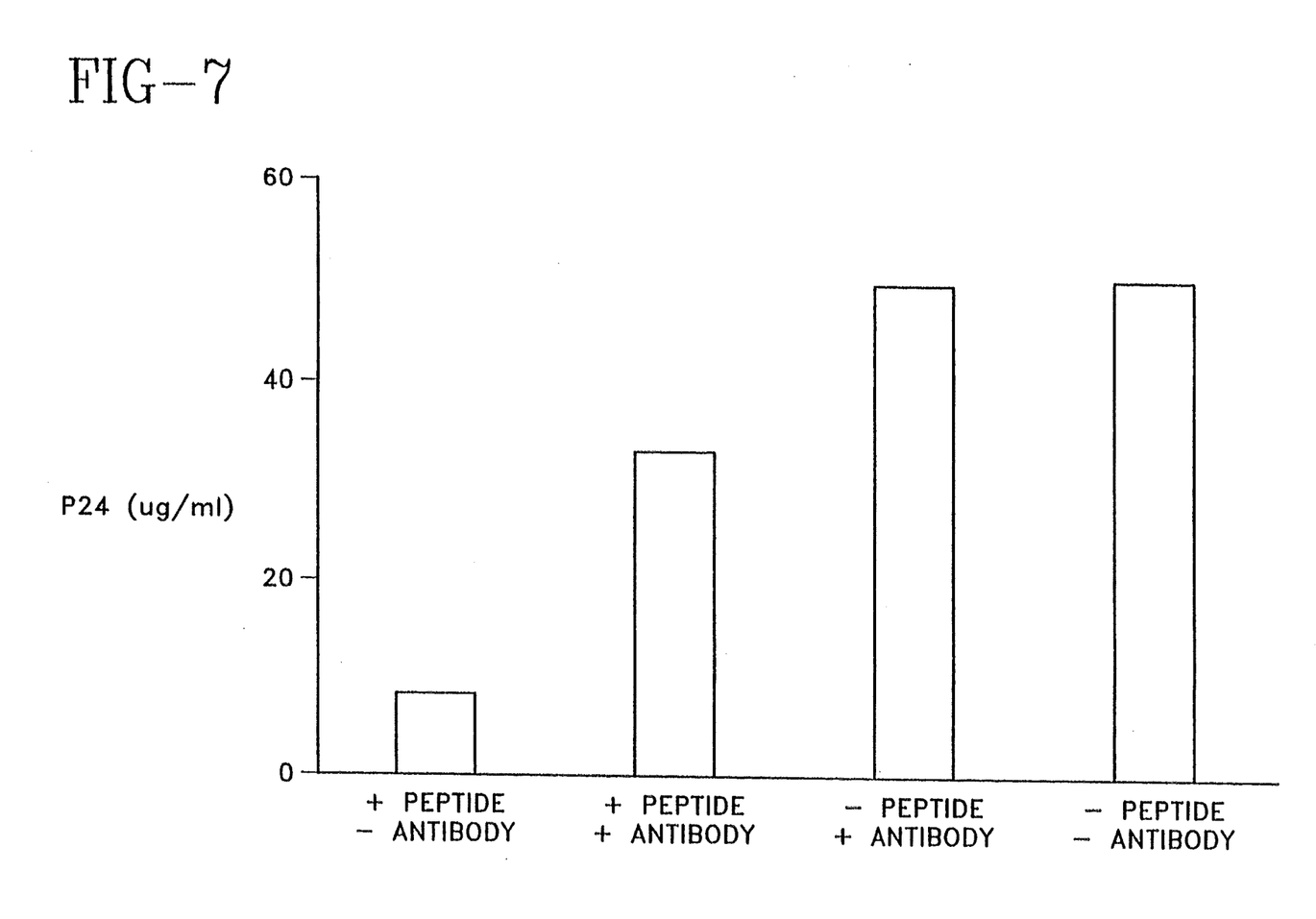
FIG. 7 illustrates that antiserum to synthetic peptide (637–666) blocks its antiviral activity.

Additionally, experiments were performed to determine whether or not the anti-HIV activity of the peptide (637–666) could be blocked by antibodies. Rabbit antiserum directed against this peptide was prepared. Serial dilutions of rabbit anti-(637–666) antiserum were incubated with the peptide (637–666) at a final concentration of 1 μg/ml at 37° C. for 30 minutes. The mixture was tested for antiviral activity. As shown in FIG. 7, in the absence of the antiserum, the peptide (637–666) significantly inhibited p24 production. However, after incubation with the anti-peptide (637–666) antiserum, the inhibitory activity of the peptide (637–666) was significantly blocked, while the antiserum alone did not affect p24 production. This result indicates that the inhibitory activity was indeed mediated by the peptide (637–666).

EXAMPLE 7

The aforementioned peptide (637–666) of the present invention was synthesized with a Gly-Gly-Cys amino acid triplet coupled at the C-terminus of the peptide.

Mass spectrometric data demonstrated that this peptide was completely dimerized. The dimerized form of the peptide will spontaneously form via the thiol group in the cysteine if allowed to incubate accordingly. The synthetic peptide was cleaved from resin stored from the original peptide synthesis and was shown to be in monomeric form using mass spectrometry. To determine the anti-HIV activity of the monomeric peptide (637–666), as compared with the anti-HIV activity of the dimeric peptide (637–666), the two peptide batches were assayed in a comparative experiment.

Figure 8:
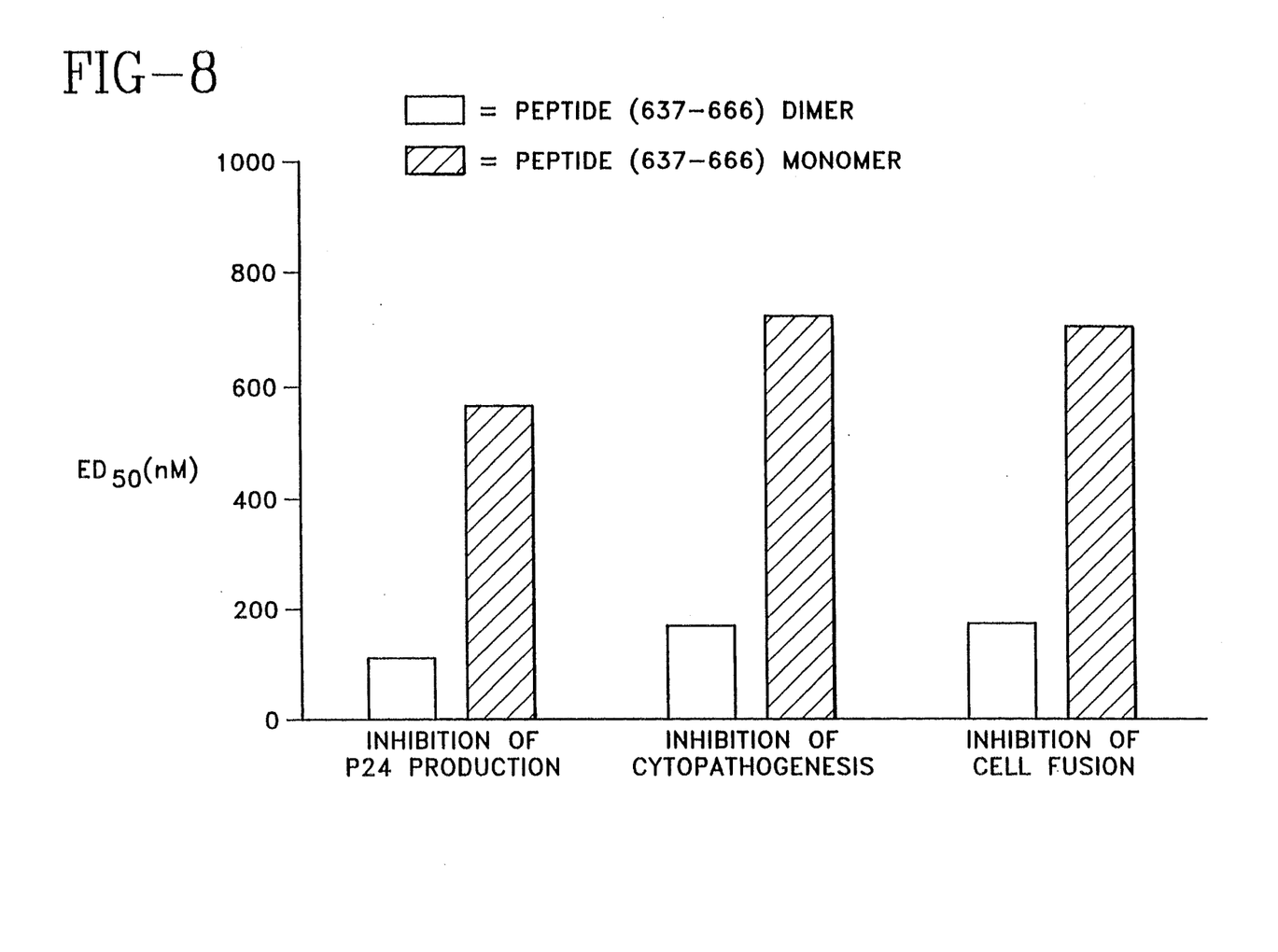
FIG. 8 illustrates a comparison of monomers and dimers of synthetic peptide (637–666) as inhibitors of HIV-1 infection.

The results of the comparative assay are shown in FIG. 8. The dimerized form of the peptide is much more effective for inhibiting HIV-1 replication, HIV-1-mediated cytopathogenesis and cell fusion than the monomeric version of the same peptide. This result suggests that the peptide (637–666) will dimerize or polymerize by the addition of an extra amino acid residue, such as cysteine, at the C-terminus or the N-terminus of the peptide. Furthermore, these results also indicate that the dimerized or polymerized form of the peptide (637–666) may more effectively interfere with the process of HIV-1 infection than the monomeric version.

As illustrated in the foregoing Examples, the polypeptide of the present invention inhibited HIV-1$_{IIIB}$ replication, HIV-1-mediated cytopathogenesis and cell fusion. Moreover, it inhibited the replication of HIV-1 in a dose-dependent manner. Its 50% effective dose (ED$_{50}$) for inhibition of HIV-1 replication was 101.0 nM. Its 50% effective dose for inhibition of cytopathogenesis mediated by HIV-1 was 142.0 nM. Its $ED_{50}$ for inhibition of cell fusion mediated by HIV-1$_{IIIB}$ infected H9 cells was 160.0 nM. Its effective concentration is lower than that of most antiviral agents tested for inhibition of HIV-1 infection, such as aurintricarboxylic acid (ATA), and hemin. This agent had very low cytotoxicity. The 50% cytotoxic dose ($CD_{50}$), determined by a colorimetric assay, is larger than 11,145 nM. Therefore, its selective index (S.I.=$CD_{50}/ED_{50}$) is more than 110.0 for inhibition of HIV-1$_{IIIB}$ replication, 78.0 for inhibition of HIV-1$_{IIIB}$-mediated cytopathogenesis and 70.0 for inhibition of HIV-1$_{IIIB}$-mediated cell fusion.

Additionally, the peptide of the present invention inhibited the replication of not only the homologous HIV-1 isolate (IIIB), but also heterologous HIV-1 isolates tested (MN, RF, and SF2). It also effectively inhibited infection by an AZT-resistant mutant which could not be effectively neutralized by AZT. The viral inhibitory activity of the peptide was blocked by rabbit antiserum directed against this synthetic peptide, suggesting that the virus-inhibitory activity is specifically mediated by the peptide (637–666) and not by other factors which may have contaminated the peptide preparation during peptide synthesis. The peptide of the present invention can dimerize, thereby enhancing its activity against HIV-1 infections.

Consequently, the polypeptide of the present invention is an ideal candidate for an antiviral agent against HIV-1, since it has a higher antiviral activity against many HIV-1 isolates than most other anti-HIV agents. The toxicity of this peptide for lymphocytes and monocytic cells is very low, suggesting that any adverse effects on human subjects may be also lower than that of currently used anti-HIV drugs, such as AZT.

AS a result, the polypeptide of the present invention provides for a method of treating HIV-1 infected subjects in addition to inhibiting viral replication in vitro. In particular, the method includes administering the polypeptide of the present invention in an amount effective to inhibit viral replication, and preferably in an amount effective to inhibit HIV-1-mediated cytopathogenesis and cell fusion. Most preferably, the amount of polypeptide administered to the subject should be sufficient to maintain an effective blood serum concentration ranging from about 0,005 mg/ml–0.01 mg/ml.

Suitable methods of administration would include any pharmacologically acceptable approaches known in the art for delivering a therapeutic or prophylactic agent, such as oral, rectal, nasal, topical (including buccal and sub-lingual), vaginal, parenteral (including intramuscular, sub-cutaneous and intravenous), as well as approaches utilizing inhalation. Additionally, the polypeptide can be incorporated into an antiviral substance containing other active ingredients, such as AZT.

While there have been described what are presently believed to be the preferred embodiments of the present invention, those skilled in the art will realize that changes and modifications may be made thereto without departing from the spirit of the invention, and it is intended to claim all such changes and modification as fall within the true scope of the invention.

---

We claim:

1. A prophylactic method of topically inhibiting HIV-1 infectivity or replication, comprising:
   topically administering to a subject an effective amount of a prophylactic antiviral substance, wherein said prophylactic antiviral substance includes:
   an HIV-1-based polypeptide having an amino acid sequence of the envelope glycoprotein of HIV-1$_{IIIB}$ or a natural variant thereof from amino acid 600 to amino acid 862, or a portion thereof containing the sequence from amino acid residue 637 to amino acid residue 666.

2. The prophylactic method of claim 1, wherein said polypeptide is attached to a carrier molecule or linking moiety capable of forming dimers of said polypeptide.

3. The prophylactic method of claim 2, wherein said polypeptide is included in dimeric form.

4. The prophylactic method of claim 1, wherein said polypeptide further comprises a Gly-Gly-Cys amino acid triplet coupled at the C-terminus of the polypeptide.

5. The prophylactic method of claim 4, wherein said polypeptide is included in a dimeric form.

6. The prophylactic method of claim 1, wherein said polypeptide has an amino acid sequence of the envelope glycoprotein of HIV-$1_{IIIB}$ is or a natural variant thereof from amino acid residue 620 to amino acid residue 680, or a portion thereof containing the sequence from amino acid residue 637 to amino acid residue 666.

7. The prophylactic method of claim 1, wherein said polypeptide has an amino acid sequence of the envelope glycoprotein of HIV-$1_{IIIB}$ or a natural variant thereof from amino acid residue 637 to amino acid residue 666.

8. The prophylactic method of claim 1, wherein said polypeptide is selected from the group consisting of SEQ ID NOS: 1, 2, 3, 4, 5, 6, 7, 8, 9, 10, 11, 12, 13, 14, 15, 16, 17, 18, 19, and 20.

9. The prophylactic method of claim 1, wherein said prophylactic antiviral substance further comprises a pharmacologically acceptable carrier.

10. The prophylactic method of claim 1, wherein said prophylactic antiviral substance further comprises another pharmacologically acceptable active ingredient.

11. An antiviral substance, comprising an HIV-1-based polypeptide having an amino acid sequence of the envelope glycoprotein of HIV-$1_{IIIB}$ or a natural variant thereof from amino acid 600 to amino acid 862, or a portion thereof containing amino acid residue 637 to amino acid residue 666.

12. The antiviral substance of claim 11, wherein said polypeptide is attached to a carrier molecule or linking moiety capable of forming dimers of said polypeptide.

13. The antiviral substance of claim 12, wherein said polypeptide is included in dimeric form.

14. The antiviral substance of claim 11, wherein said polypeptide further comprises a Gly-Gly-Cys amino acid triplet coupled at the C-terminus of the polypeptide.

15. The antiviral substance of claim 14, wherein said polypeptide is included in a dimeric form.

16. The antiviral substance of claim 11, wherein said polypeptide has an amino acid sequence of the envelope glycoprotein of HIV-$1_{IIIB}$ or a natural variant thereof from amino acid residue 620 to amino acid residue 680, or a portion thereof containing amino acid residue 637 to amino acid residue 666.

17. The antiviral substance of claim 11, wherein said polypeptide has an amino acid sequence of the envelope glycoprotein of HIV-$1_{IIIB}$ is or a natural variant thereof from amino acid residue 637 to amino acid residue 666.

18. The antiviral substance of claim 11, wherein said polypeptide is selected from the group consisting of SEQ ID NOS: 1, 2, 3, 4, 5, 6, 7, 8, 9, 10, 11, 12, 13, 14, 15, 16, 17, 18, 19, and 20.

19. The antiviral substance of claim 11, wherein said prophylactic antiviral substance further comprises a pharmacologically acceptable carrier.

20. The antiviral substance of claim 11, wherein said prophylactic antiviral substance further comprises another pharmacologically acceptable active ingredient.

* * * * *